United States Patent [19]

Misawa et al.

[11] Patent Number: 5,189,189
[45] Date of Patent: Feb. 23, 1993

[54] METHOD OF PURIFYING POLYUNSATURATED ALIPHATIC COMPOUNDS

[75] Inventors: Yoshihisa Misawa; Hisao Kondo; Tetsuya Tsutsumi; Masahiro Hayashi; Daisuke Sugimori, all of Tsukuba; Yorishige Matsuba, Kakogawa; Masashi Isozaki, Kakogawa; Hiroharu Nishigaki, Kakogawa; Kazunaga Yazawa, Sagamihara; Kiyosi Kondo, Yamato, all of Japan

[73] Assignees: Harima Chemicals, Inc., Kakogawa; Sagami Chemical Research Center, Tokyo, Japan

[21] Appl. No.: 689,622

[22] Filed: Apr. 23, 1991

[30] Foreign Application Priority Data

Apr. 24, 1990 [JP] Japan ................. 2-106503
Oct. 19, 1990 [JP] Japan ................. 2-282579
Oct. 24, 1990 [JP] Japan ................. 2-284249
Jan. 28, 1991 [JP] Japan ................. 3-025126

[51] Int. Cl.$^5$ ............................. C11B 7/00
[52] U.S. Cl. ............................... 554/194
[58] Field of Search .............. 260/428, 428.8; 554/189, 194; 522/256

[56] References Cited

U.S. PATENT DOCUMENTS 3,960,976 6/1976 Suzuki et al. ............ 260/674

OTHER PUBLICATIONS

Chemical Abstracts, vol. 110, #5, 1989, p. 102, 40 789k.

*Primary Examiner*—Jose' G. Dees
*Assistant Examiner*—Deborah D. Carr
*Attorney, Agent, or Firm*—Cushman, Darby & Cushman

[57] ABSTRACT

[Object] A fatty acid-related polyunsaturated compound can be selectively purified using an industrially operable successive method under moderate conditions. [Content] A highly purified fatty acid-related polyunsaturated compound is obtained by a process comprising steps of forming a complex with silver on account of the high degree of unsaturation of the fatty acid-related polyunsaturated compound, isolating the complex from other fats on account of the hydrophilicity of the complex and then applying dissociating procedures to the complex to obtain the fatty acid-related polyunsaturated compound as a target substance on account of the hydrophobicity of the fatty acid-related polyunsaturated compound. As to the procedures for dissociation, addition of a dissociating agent and reduction of silver are disclosed. As to the dissociating agent, various compounds which produce insoluble composition with silver other then water are disclosed. Furthermore, an apparatus appropriately used to carry out this method is also disclosed.

13 Claims, 1 Drawing Sheet

1

METHOD OF PURIFYING POLYUNSATURATED ALIPHATIC COMPOUNDS

FIELD OF THE INVENTION

The present invention relates to a method of obtaining a highly purified, polyunsaturated aliphatic compound (hereinafter referred to as a fatty acid-related polyunsaturated compound) having an degree of unsaturation of 3 or more, such as polyunsaturated fatty acids, esters and acid amides thereof and polyunsaturated alcohols having an unsaturation degree of 3 or more and, particularly to a method of selectively extracting, isolating and purifying a fatty acid-related polyunsaturated compound having an unsaturation degree of 3 or more, such as fatty acid-related polyunsaturated compounds, e.g., eicosapentaenoic acid and docosahexaenoic acid which are contained in oils or fats of fish such as mackerel or sardine, and derivatives thereof, fatty acid-related polyunsaturated compounds, such as arachidonic acid, which are contained in oils or fats of animals such as pigs, and derivatives thereof, fatty acid-related polyunsaturated compounds, such as α-linolenic and γ-linolenic acids, which are contained in oils or fats of plants, and derivatives thereof, and furthermore, fatty acid-related polyunsaturated compounds, which are derived from algae and microorganisms, and derivatives thereof, selectively and effectively at a low cost and furthermore practically on an industrial scale without causing denaturation or degeneration during the processes of extraction, isolation and purification.

DESCRIPTION OF THE PRIOR ART

Examples of known methods of extracting, isolating and purifying fatty acid-related polyunsaturated compounds include an urea adduct method, a molecular distillation method, a solvent fractionation method and a chromatographic method. However, these methods are entirely disadvantageous to isolate and purify the fatty acid-related polyunsaturated compounds and esters thereof in a high purity and in a large amount at a low cost without causing denaturation. For example, the fatty acid-related polyunsaturated compounds and esters thereof obtained by the urea adduct method are poor in their purity and those obtained by the molecular distillation method tend to be readily denatured by polymerization or isomerization; the solvent fractionation method and the chromatographic method are generally not applicable to the isolation and purification on a large scale practically for industrial production.

Furthermore, it is generally known that silver ion becomes attached to an organic compound through unsaturated linkages to form a complex. Using this property of complexation, methods of purifying the fatty acid-related polyunsaturated compounds such as eicosapentaenoic acid or esters thereof are disclosed, for example, in Japanese Patent Laid-open No. 208549/1988, in which silver ion is immobilized on an adsorptive agent and then the difference in affinity between silver and the fatty acid-related polyunsaturated compounds is advantageously used.

SUMMARY OF THE INVENTION

An object of the present invention is to provide a method of purifying a fatty acid-related polyunsaturated compound by first forming a complex of silver with a material containing the fatty acid-related polyunsaturated compound, removing other undesirable compounds on account of hydrophilic property of the complex, releasing the fatty acid-related polyunsaturated compound from the complex by means of dissociation and then purifying the target compound on account of its hydrophobic property. A further object of the present invention is to provide an apparatus to be appropriately used for this method.

DETAILED DESCRIPTION OF THE PREFERRED EMBODIMENT

Figure 1A:
FIGS. 1(a) and 1(b) are a plain view and a sectinal front view schematically illustrating a bulk liquid membrane apparatus to carry out embodiments of the present invention. 1 and 2 represent solvents, 3 represents a bulk liquid membrane, 4 represents an separation cell, 5 represents a partition board, 6 represents a holder and 7 represents a supported liquid membrane.

Based on the above-mentioned prior art, the present inventors found that only fatty acid-related polyunsaturated compounds can be selectively extracted, isolated and purified on an industrial scale by a process wherein a material containing a target fatty acid-related polyunsaturated compound is stirred with a silver salt, which is capa ble of forming a complex through unsaturated bonds, is dissolved in an aqueous medium solution at above a certain concentration so that only the fatty acid-related polyunsaturated compound having an unsaturated degree of 3 or more forms a complex, i.e. [the silver salt soluble in the aqueous medium - the fatty acid-related polyunsaturated compound], to be extracted in the aqueous medium phase, and after fractionation of the aqueous medium phase, the complex in the aqueous medium phase is subjected to dissociation procedures, and thus completed the present invention.

The fatty acid-related polyunsaturated compounds in the present invention, as defined above, include ester-type derivatives such as methyl esters, ethyl esters, triglycerides, diglycerides and monoglycerides, carboxylic acid-type derivatives such as amides and methyl amides and aliphatic alcohols. Furthermore, the fatty acid- related polyunsaturated compounds herein mean fatty acid- related compounds having an degree of unsaturation of 3 or more.

In the present invention, a silver salt, which is capable of forming a complex through unsaturated linkages, dissolved in an aqueous medium is added to a material containing a fatty acid-related polyunsaturated compound, and the resultant mixture is stirred for 5 minutes to 4 hours so that a complex, i.e. [silver salt - the fatty acid-related polyunsaturated compound], which is soluble in the aqueous medium, is formed, and only the fatty acid-related polyunsaturated compound having an degree of unsaturation of 3 or more can be selectively dissolved in the aqueous medium phase. In this case, the reaction may be carried out at any low temperature as far as the solution remains to be liquid or at a temperature at the upper limit as high as 100° C., but preferably at near room temperature considering the stability of the fatty acid-related polyunsaturated compound, the solubility of the silver salt in water and the rate of complex formation. The reaction time is preferably 10 minutes to 2 hours. Furthermore, considering the oxidation stability of the fatty acid-related polyunsaturated compound and the stability of the silver salt, all procedures in the present invention are preferably carried out in the dark under an atmosphere of inert gas such as nitrogen and argon. As to the silver salt which is capable of forming a complex through unsaturated linkages, any silver salt may be used; in general, silver compounds, which are soluble in an aqueous medium, such as silver nitrate, silver perchlorate, silver acetate and silver tetra fluoroborate are used. The aqueous medium as used in the present invention denotes water and compounds having hydroxyl groups, such as glycerin and ethylene glycol. The mixtures of these compounds may also be used in the present invention. The present invention can be effectively carried out at a molar ratio of a fatty acid-related polyunsaturated compound to a silver salt in the range between 1:100 and 100:1 and at a concentration of the silver salt in the range between 0.1 mol per liter and saturation. At a concentration lower than this range, complex formation is not satisfactory enough to make the fatty acid-related polyunsaturated compound soluble in the aqueous medium. Considering recovery of the fatty acid-related polyunsaturated compound, the molar ratios between 1:5 and 1:1 and the concentrations between one mole and 20 moles per liter are preferable.

The complex formed in the above-mentioned process is present in the aqueous medium phase and can be isolated exclusively from the reaction system by mechanically separating the aqueous medium phase and the oil and fat phase or by extracting the oil and fat phase using an organic solvent to remove other undesirable fatty acidrelated compounds. The organic solvent to be used in this case is that which can be separable from water, such as hexane and ether. The aqueous medium phase separated in this procedure includes a complex, i.e. [silver salt — fatty acid-related polyunsaturated compound]. By subjecting the complex in the aqueous medium phase to the dissociation procedure, the target fatty acid-related polyunsaturated compound is released and can be recovered by lowering the solubility in the aqueous medium. Examples of the procedure to dissociate the complex include a method in which an agent for dissociating the complex is added to dissociate the complex, in particular, a method in which the complex is dissociated by dilution with water, a method in which the complex is extracted by using an organic solvent which is separable from the aqueous medium, a method in which heating is applied and a method in which the complex is dissociated by reducing silver ion to silver. These methods will be discussed more in detail hereinafter.

Dissociation of a complex by a complex dissociating agent can be accomplished with the use of the complex dissociating agent by replacing a fatty acid-related polyunsaturated compound forming a complex with silver so that the complex dissociating agent alternatively forms a silver compound with silver. Generally speaking, any complex dissociating agent which is highly active in dissociating the complex can be used. Preferable examples of the complex dissociating agent are oxygen-related compounds which include alcohols such as ethylene glycol, glycerin and diethylene glycol, ethers such as 1,4-dioxane, tetrahydrofuran and crown ether and carbonyls such as acetone; nitrogen-related compounds which include amines such as ammonia, isobutylamine, ethylenediamine, diethylamine, triethylamine, pyridine and piperidine, amides such as dimethylformamide and N-methylpyrrolidine, nitrils such as acetonitrile, ammonium salts and amine salts; sulfur-related compounds which include thiols such as 1,2-ethandithiol, sulfides such as diphenylsulfide and tetrahydrothiophene, sulfoxides such as dimethylsulfoxide and sulfones such as sulfolane; phosphorus-related compounds such as triatomic phosphorus compounds such as triphenylphosphine, pentaatomic phosphorus compounds such as phosphate, e.g., trimethylphosphate, hexamethylphosphate triamide and other phosphates, arsenic compounds such as triphenylarsine and antimony compounds; $\pi$-electron binding ligands such as carbon monoxide, isocyanides and nitric monoxide; compounds having functional multiple bond(s) capable of forming a complex, which include alkenes such as ethylene, cyclohexene, 2-methyl-2-butene and isoprene; alkenes; alkynes; aromatic compounds; compounds which form silver compounds insoluble in an aqueous medium; silver ion; or compounds capable of interfering with complex formation of silver ion with a fatty acid-related polyunsaturated compound, and ions thereof which include halogenides such as sodium chloride and sodium bromide, sulfates such as sodium sulfate, sulfites, nitrates, thiosulfates, carbonates such as sodium carbonate, salts of carboxylic acid such as sodium tartrate, and sodium acetate thiocyanates such as ammonium thiocyanate, cyanates, azides such as sodium azide, permanganates and acid-type compounds thereof, hydroxide compounds such as sodium hydroxide, and multi-functional compounds having two or more of the above-mentioned functional groups. Further, these compounds can be used in mixture.

Dissociation of the complex by dilution is carried out by adding an aqueous medium additionally to the aqueous medium phase for dilution to release the fatty acid-related polyunsaturated compound. The aqueous medium for dilution may be used in quantity enough to cause dissociation of the complex; however, generally, the amount more than equivalent, preferably 10- to 40-folds, is used. An organic solvent used for the aqueous medium containing the formed complex consisting of the fatty acid-related polyunsaturated compound and silver is used to extract the fatty acid-related polyunsaturated compound. Examples of the organic solvents to be used include those which are separable from the aqueous phase, such as hexane, ether, ethyl acetate, benzene, chloroform, dichloromethane, carbon tetrachloride, dichloroethane, cyclohexane, toluene, xylene and butyl acetate. These are used in quantity 1- to 100-fold, preferably 5- to 40-fold, of the aqueous phase.

Dissociation of the complex by heating may be carried out at a temperature higher than that used for forming the complex; however, it may be carried out at near the boiling point of the medium.

Furthermore, the complex can be dissociated by reducing the silver ion to silver using a reducing agent such as sodium borohydride, electrolysis or light.

Considering recycling of the silver salt, the method by diluting with water is advantageous.

The released fatty acid-related polyunsaturated compound can be extracted and recovered using an organic solvent, such as hexane and ether, which is separable from the aqueous medium and silver ion can be removed by washing the fractionated organic solvent phase with water and saturated saline.

Furthermore, the aqueous medium is removed from the aqueous medium phase containing silver ion and thus the silver salt can be recovered for recycling.

Furthermore, according to the present invention, the purity of the fatty acid-related polyunsaturated compound can be furthermore improved by repeating the abovementioned isolation and purification procedures.

The present invention thus provides a method of extracting, isolating and purifying a fatty acid-related polyunsaturated compound selectively on an industrial scale from a material containing the fatty acid-related polyunsaturated compound, as mentioned above, wherein first a complex is formed on account of capability of a silver salt, in forming a complex with the fatty acid- related polyunsaturated compound through unsaturated linkages and then a fraction containing the fatty acid-related polyunsaturated compound only can be selectively isolated on account of the solubility of the complex in the aqueous medium, and lastly the complex is dissociated to release the fatty acid-related polyunsaturated compound.

Details of the method for purification according to the present invention are explained above; now an apparatus to be appropriately used for embodying the purification method of the invention will be explained as follows:

The apparatus for purification according to the present invention is that in which a liquid membrane method is applied.

The present inventors investigated the liquid membrane method in which an aqueous medium solution of a silver compound is used as a liquid membrane and found that using this method fatty acid-related polyunsaturated compounds can be selectively and effectively isolated without any additional steps for dissociation, thereby completing the purification apparatus of the present invention. Namely, the purification apparatus of the present invention comprises a liquid membrane consisting of an aqueous medium containing a silver salt and two solvents, which are immiscible with the liquid membrane, each separately retained or circulated in a cell sectioned by the liquid membrane; a mixture containing a target fatty acid-related polyunsaturated compound is supplied into one of the two solvents so that the fatty acid-related polyunsaturated compound is selectively transported via the liquid membrane into the other solvent to be recovered.

The membrane method as used herein is a method for separation described in Chemical Engineering Dictionary (third edition, edited by The Society of Chemical Engineerings, Japan, Maruzen Co., Ltd.), wherein a solvent which selectively dissolves a target component or a solvent containing an agent which selectively reacts with the target component is made into a liquid membrane, the liquid membrane partitions the two other phases which are immisicible with the liquid membrane so that the target component permeates through the liquid membrane to be isolated and concentrated. The liquid membrane is made in various forms such as a bulk liquid membrane, a supported liquid membrane and an emulsified liquid membrane. In particular, for example, a method using the bulk liquid membrane will be explained in more detail with reference to FIG. 1 as follows: A cell 4 is partitioned by a partition board 5 so as to pass fluid through at the bottom and an aqueous medium solution of a silver compound is poured into the cell up to a level so that an opening for passage 5a is blocked to form a liquid membrane 3. Thereafter, two kinds of solvents 1 and 2 which are immiscible with the liquid membrane 3 are placed separately in the sides partitioned by the partition board 5. A mixture containing a target fatty acid-related polyunsaturated compound is dissolved in one of the two solvents and the solvent 1, the solvent 2 and the content of liquid membrane 3, all or one of them, are gently stirred. The stirring is carried out to facilitate transportation of substance and should not be too vigorous not to brake the liquid membrane or intermix the two solvent phases via the liquid membrane. As the stirring is continued, the fatty acid-related polyunsaturated compound forming a complex passes through the liquid membrane 3 from the side of solvent 1 containing the mixture and be extracted into the solvent 2 on the other side. After several hours, the solvent phase is recovered and the solvent is removed to selectively obtain the target fatty acid-related polyunsaturated compound. Furthermore, the both of the solvents 1 and 2 are successively supplied while the fluid in an equivalent amount is excluded so that the operation can be successively continued.

Figure 2:
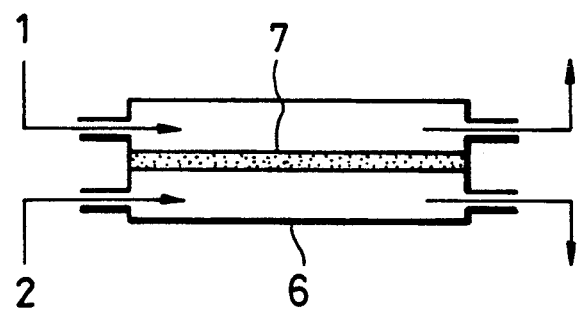

In the case of the supported liquid membrane method as shown in FIG. 2, the inside of a rectangular holder 6 for a flat sheet membrane is divided into upper and lower compartments by a supported liquid membrane 7. An aqueous medium solution of a silver compound is formed by absorption in a supporter. Various hydrophilic, porous materials such as cellulose acetate membrane can be used as a material for the supporter. It is essentially desirable that the porous supporter can support an aqueous medium solution firmly and has an excellent wetting affinity with the aqueous medium solution and an appropriate small pore size. In order to facilitate the mass transfer of the material inside the membrane, thinner membrane with a higher porosity are desirable. More particularly, a hydrophilic membrane material having a pore size less than one micrometer in diameter, a porosity of 60% or more and a membrane thickness of 200 micrometers or less is preferable. A mixture containing a target fatty acid-related polyunsaturated compound is dissolved in a solvent 1 which is immiscible with the liquid membrane and supplied into one side, particularly in the top, of the liquid membrane 7 and a solvent 2 which contains no solute is supplied into the other side, particularly in the bottom, of the membrane. As both solvents pass through the apparatus 6 the target fatty acid-related polyunsaturated compound forms a complex and the resulting complex permeates through the supported liquid membrane 7 from the side of solvent 1 containing the mixture and extracted into the solvent 2 on the other side. After removing the solvent from the discharged solvent phase, the target fatty acid-related polyunsaturated compound can be selectively obtained.

The liquid membrane methods to be used are not limited to the above-mentioned two methods. For example, an emulsified liquid membrane method in which a mixture containing a fatty acid-related polyunsaturated compound or a solution thereof is dispersed in an aqueous medium containing a silver compound and then the resulting fluid is further dispersed in a solvent which makes a receptor phase of the fatty acid-related polyunsaturated compound can also be used for isolation. Furthermore, in order to increase the efficiency in the supported membrane method, various kinds of apparatus, such as a spiral type or a hollow fiber module type apparatus or an apparatus for a flowing liquid membrane in which the liquid membrane flows to facilitate transportation of substances. As to the solvent, any solvent which dissolves a fatty acid-related highly-unsaturated compound and is immiscible with an aqueous medium solution may be used. Examples of these solvents include hydrocarbon solvents such as hexane, heptane and octane.

As explained above, the apparatus of the present invention is effective and extremely advantageous because the procedure for the purification of fatty acid-related polyunsaturated compounds specified in the steps 1 through 3 can be carried out continuously. The step 4 also specified in claim 1 can be substantially carried out by generally known conventional means.

The present invention will be explained more in detail with reference to the following examples. In the examples, a composition of fatty acids is analyzed by gas chromatography after methyl-esterification and, furthermore, a composition of fatty acid esters is analyzed also by gas chromatography. Conditions for the analysis were as follows:
Apparatus: GC-15A, Shimazu Seisakusho, Co., Ltd.
Column: ULBON HR-SS-10
Column temperature: 200° C.
Sample caburetion chamber/detecting temperature: 250° C.
Carrier gas: helium 1.2 ml/min (split ratio =80:1)
Hydrogen flow rate: 40 ml/min
Detector: FID

EXAMPLE 1

An aqueous solution in which 139.6 g of silver nitrate was dissolved in 80 ml of distilled water was added to 100 g of a fatty acid mixture containing 60% of eicosapentaenoic acid under an atmosphere of nitrogen in the dark. After stirring for 2 hours, the resulting reaction mixture was washed twice with one liter of hexane. Two litters of distilled water was added to the aqueous phase thus obtained and the resulting admixture was stirred for one hour so that a complex was formed to release fatty acids. The released fatty acids were extracted twice with one liter of hexane, the resulting hexane phase was washed with distilled water and saturated saline and was dehydrated with magnesium sulfate. By concentration under reduced pressure, 39.78 g of a fatty acid fraction was obtained. Analysis of the fatty acid composition showed a purity of eicosapentaenoic acid was 96.0%. Further the eicosapentaenoic acid fraction having the 96.0% purity thus obtained was purified in the same manner as described above. As a result, eicosapentaenoic acid having a purity of 98.5% was obtained.

EXAMPLE 2

An aqueous solution in which 130.9 g of silver nitrate was dissolved in 80 ml of distilled water was added to 101.1 g of a fatty acid mixture containing 54.0% of docosahexaenoic acid under an atmosphere of nitrogen in the dark and the resulting mixed solution was stirred for 2 hours. In the same manner as described in Example 1, 43.52 g of a fatty acid fraction was obtained. Analysis of the fatty acid composition of the fraction showed that docosahexaenoic acid having a purity of 92.3% was obtained. Furthermore, docosahexaenoic acid having the 96.0% purity thus obtained was purified in the same manner as described above. As a result, docosahexaenoic acid having a purity of 96.4% was obtained.

EXAMPLE 3

An aqueous solution in which 142.1 g of silver nitrate was dissolved in 80 ml of distilled water was added to 101 g of a fatty acid mixture containing 53% of arachidonic acid under an atmosphere of nitrogen in the dark and the resulting mixed solution was stirred for 2 hours. In the same manner as described in Example 1, 30.05 g of a fatty acid fraction was obtained. Analysis of the fatty acid composition of the fraction showed that arachidonic acid was obtained in a purity of 95.2%. Furthermore, arachidonic acid having the 95.2% purity thus obtained was purified in the same manner as described above. As a result, arachidonic acid having a purity of 97.0% was obtained.

EXAMPLE 4

An aqueous solution in which 1.688 g of silver nitrate was dissolved in 0.5 ml of distilled water was added to 1.012 g of a fatty acid ethyl ester mixture containing 62.1% of eicosapentaenoic acid ethyl ester under an atmosphere of nitrogen in the dark and the admixture was stirred for 2 hours. The resulting reaction mixture was washed twice with 20 ml of hexane. 20 ml of distilled water was added to an aqueous phase thus obtained and the resulting admixture was stirred for one hour so that a complex was formed to release fatty acid ethyl esters. The released fatty acid ethyl esters were extracted twice with 20 ml of hexane. The resulting hexane phase was washed with distilled water and then with saturated saline and was dehydrated using magnesium sulfate. By concentration under reduced pressure, 209.7 mg of a fatty acid ethyl ester fraction was obtained. Analysis of the fatty acid ethyl esters in the fraction showed that eicosapentaenoic acid ethyl ester was obtained in a purity of 98.0%.

EXAMPLE 5

An aqueous solution in which 1.6873 g of silver nitrate was dissolved in 0.5 ml of distilled water was added to 713.5 mg of a fatty acid ethyl ester mixture containing 59.0% of docosahexaenoic acid ethyl ester under an atmosphere of nitrogen in the dark and the admixture was stirred for 2 hours. In the same manner as described in Example 4, 251.4 mg of a fatty acid ethyl ester fraction was obtained. Analysis of the composition of the fatty acid ethyl esters thus obtained showed that the purity of docosahexaenoic acid ethyl ester was 97.0%.

EXAMPLE 6

An aqueous solution in which 1.6781 g of silver nitrate was dissolved in 0.5 ml of distilled water was added to 630.2 mg of a fatty acid ethyl ester mixture containing 52.5% of arachidonic acid ethyl ester under an atmosphere of nitrogen in the dark and the admixture was stirred for 2 hours. In the same manner as described in Example 4, 180.3 mg of a fatty acid ethyl ester fraction was obtained. Analysis of the composition of this fraction showed that the purity of arachidonic acid ethyl ester was increased to 96.3%.

EXAMPLE 7

An aqueous solution in which 1.0703 g of silver perchlorate was dissolved in 0.5 ml of distilled water was added to 670 mg of a fatty acid mixture containing 54.0% of docosahexaenoic acid under an atmosphere of nitrogen in the dark. After stirring for 2 hours, the resulting reaction mixture was washed twice with 20 ml of hexane. 20 ml of distilled water was added to the aqueous phase thus obtained and the resulting admixture was stirred for one hour so that a complex was formed to release fatty acids. The released fatty acids were extracted twice with 20 ml of hexane, the resulting hexane phase was washed with distilled water and with saturated saline and was dehydrated using magnesium sulfate. By concentration under reduced pressure, 211.9 mg of a fatty acid fraction was obtained. Analysis of the fatty acid composition showed that the purity of docosahexaenoic acid was 93.1%.

EXAMPLE 8

Hog-liver oil which was obtained from the liver of hogs by a conventional method was saponified to obtain a preparation of hog-liver-oil free fatty acids. This preparation contained 14.3% of arachidonic acid. An aqueous solution in which 1.128 g of silver perchlorate was dissolved in 0.5 ml of distilled water was added under an atmosphere of nitrogen in the dark to 1.058 g of this fatty acid preparation dissolved in 0.5 ml of hexane. After stirring for one hour, the resulting reaction mixture was washed twice with 20 ml of hexane. 20 ml of distilled water was added to the aqueous phase thus obtained and the resulting admixture was stirred for one hour so that a complex was formed to release fatty acids. The released fatty acids were extracted twice with 20 ml of hexane, the resulting hexane phase was washed with distilled water and with saturated saline and was dehydrated using magnesium sulfate. By concentration under reduced pressure, 70.8 mg of fatty acids was obtained. Analysis of the fatty acid composition showed that the purity of arachidonic acid was 76.4%.

EXAMPLE 9

Linseed oil obtained by a conventional method was saponified to obtain a preparation of linseed-oil free fatty acids. This preparation contained 55.8% of α-linolenic acid. An aqueous solution in which 920 mg of silver perchlorate was dissolved in 0.5 ml of distilled water was added under an atmosphere of nitrogen in the dark to 1.013 g of this fatty acid preparation dissolved in 0.5 ml of hexane. After stirring for one hour, the resulting reaction mixture was washed twice with 20 ml of hexane. 20 ml of distilled water was added to the aqueous phase thus obtained and the resulting admixture was stirred for one hour so that a complex was formed to release fatty acids. The released fatty acids were extracted twice with 20 ml of hexane, the resulting hexane phase was washed with distilled water and with saturated saline and was dehydrated using magnesium sulfate. By concentration under reduced pressure, 150 mg of fatty acids was obtained. Analysis of the fatty acid composition showed that the purity of α-linolenic acid was increased to 98.2%.

EXAMPLE 10

Borage oil was saponified by an ordinary method to obtain a preparation of BOREJJI-oil free fatty acids. This preparation contained 23.1% of γ-linolenic acid. An aqueous solution in which 809 mg of silver perchlorate was dissolved in 0.5 ml of distilled water was added under an atmosphere of nitrogen in the dark to 1.037 g of this fatty acid preparation dissolved in 0.5 ml of hexane. After stirring for one hour, the resulting reaction mixture was washed twice with 20 ml of hexane. 20 ml of distilled water was added to the aqueous phase thus obtained and the resulting admixture was stirred for one hour so that a complex was formed to release fatty acids. The released fatty acids were extracted twice with 20 ml of hexane, the resulting hexane phase was washed with distilled water and with saturated saline and was dehydrated using magnesium sulfate. By concentration under reduced pressure, 59.7 mg of fatty acids was obtained. Analysis of the fatty acid composition showed that the purity of γ-linolenic acid was increased to 93.4%.

EXAMPLE 11

Purified fish-oil (triglyceride-type containing 16.7% of eicosapentaenoic acid and 11.9% of docosahexaenoic acid) 5.277 g was added under an atmosphere of nitrogen in the dark to an aqueous solution in which 853 mg of silver nitrate was dissolved in 0.5 ml of distilled water. After stirring for one hour, the resulting reaction mixture was washed twice with 20 ml of hexane. 20 ml of distilled water was added to the aqueous phase thus obtained and the resulting admixture was stirred for one hour so that a complex was formed to release triglycerides. The released triglycerides were extracted twice with 20 ml of hexane and the resulting hexane phase was washed with distilled water and then with saturated saline and was dehydrated using magnesium sulfate. By concentration under reduced pressure, 85.8 mg of triglycerides was obtained. Analysis of the fatty acid composition showed that the purity of eicosapentaenoic acid and docosahexaenoic acid was increased to 38.5% and 24.0%, respectively.

EXAMPLE 12

An aqueous solution in which 852 mg of silver nitrate was dissolved in 0.5 ml of distilled water was added under an atmosphere of nitrogen in the dark to a solution in which 1.005 g of an aliphatic alcohol mixture containing 45% of docosahexaenol was dissolved in 0.5 ml of hexane. After stirring for one hour, the resulting reaction mixture was washed twice with 20 ml of hexane. 20 ml of distilled water was added to the aqueous phase thus obtained and the resulting admixture was stirred for one hour so that a complex was formed to release aliphatic alcohols. The released aliphatic alcohols were extracted twice with 20 ml of hexane and the resulting hexane phase was washed with distilled water and then with saturated saline and was dehydrated using magnesium sulfate. By concentration under reduced pressure, 145 mg of an aliphatic alcohol fraction was obtained. Analysis of the composition showed that the purity of docosahexaenol in the fraction was 98.5%.

EXAMPLE 13

An aqueous solution in which 847.2 mg of silver nitrate was dissolved in 0.5 ml of distilled water was added under an atmosphere of nitrogen in the dark to a solution in which 1.003 g of a fatty acid mixture containing 60% of eicosapentaenoic acid was dissolved in 0.5 ml of hexane. After stirring for 2 hours, the resulting reaction mixture was washed twice with 20 ml of hexane. 20 ml of ethylene glycol as a complex dissociating agent was added to the aqueous phase thus obtained and the resulting admixture was stirred for one hour so that a complex was formed to release fatty acids. The released fatty acids were extracted twice with 20 ml of hexane and the resulting hexane phase was washed with distilled water and then with saturated saline and was dehydrated using magnesium sulfate. By concentration under reduced pressure, 133.8 mg of fatty acids was obtained. Analysis of the fatty acid composition showed that the purity of eicosapentaenoic acid was 94.4%.

EXAMPLE 14

An aqueous solution in which 845.2 mg of silver nitrate was dissolved in 0.5 ml of distilled water was added under an atmosphere of nitrogen in the dark to a solution in which 1.010 g of a fatty acid mixture containing 60% of eicosapentaenoic acid was dissolved in 0.5 ml of hexane. After stirring for 2 hours, the resulting reaction mixture was washed twice with 20 ml of hexane. 1.05 g of sodium chloride as a complex dissociating agent was added to the aqueous phase thus obtained and the resulting admixture was stirred for one hour so that a complex was formed to release fatty acids. The released fatty acids were extracted twice with 20 ml of hexane and the resulting hexane phase was washed with distilled water and then with saturated saline and was dehydrated using magnesium sulfate. By concentration under reduced pressure, 150.6 mg of fatty acids was obtained. Analysis of the fatty acid composition showed that the purity of eicosapentaenoic acid was 93.1%.

EXAMPLES 15 to 49

Various compounds which form a water insoluble compositions with various kinds of silver were tested for their activity as complex dissociating agents. As a result, the purity of the obtained fatty acid-related highlyunsaturated compounds was shown in Table 1.

Experimental conditions were the same as described in Example 1 using a starting material containing 1 g of eicosapentaenoic acid or in Example 4 using a starting material containing 1 g of eicosapentaenoic acid ethyl ester.

TABLE 1

| Example | Material | Dissociating agent | Amount | Purity (%) |
|---|---|---|---|---|
| 15 | B* | Methanol | 20 ml | 87.5 |
| 16 | A* | Sodium chloride | 1 g | 94.2 |
| 17 | A | Acetone | 20 ml | 79.6 |
| 18 | A | Sodium bromide | 1 g | 89.9 |
| 19 | A | Dimethylformamide | 20 ml | 90.1 |
| 20 | A | Dimethyl sulfoxide | 20 ml | 89.7 |
| 21 | A | Ethylene glycol | 20 ml | 95.7 |
| 22 | A | Glycerin | 20 ml | 94.4 |
| 23 | A | Diethylene glycol | 20 ml | 95.9 |
| 24 | A | Acetonitrile | 20 ml | 86.3 |
| 25 | A | 1,4-Dioxane | 20 ml | 90.0 |
| 26 | B | Isobutylamine | 20 ml | 96.7 |
| 27 | B | Ethylenediamine | 20 ml | 97.1 |
| 28 | B | Ammonia | (blow in) | 93.9 |
| 29 | B | Diethylamine | 5 ml | 96.5 |
| 30 | B | Triethylamine | 5 ml | 97.6 |
| 31 | B | Pyridine | 5 ml | 96.6 |
| 32 | A | Acetic acid | 0.5 ml | 82.0 |
| 33 | B | Piperidine | 2 ml | 94.6 |
| 34 | A | Hexamethylphosphate triamide | 2 ml | 92.8 |
| 35 | A | Tetrahydrofuran | 5 ml | 90.4 |
| 36 | A | Triphenylphosphine | 500 mg | 95.1 |
| 37 | A | Sodium acetate | 500 mg | 96.8 |
| 38 | A | Tetrahydrothiophene | 2 ml | 96.3 |
| 39 | A | Trimethyl phosphate | 3 ml | 87.0 |
| 40 | A | N-Methylpyrrolidone | 5 ml | 91.7 |
| 41 | A | Sodium sulfate | 500 mg | 93.3 |
| 42 | A | Sodium carbonate | 500 mg | 92.1 |
| 43 | A | Ammonium thiocyanate | 500 mg | 96.4 |
| 44 | A | Sodium azide | 500 mg | 95.3 |
| 45 | A | Sodium tartrate | 500 mg | 95.0 |
| 46 | A | Isoprene | 5 ml | 90.1 |
| 47 | A | Cyclopentene | 5 ml | 86.1 |
| 48 | A | 2-Methyl-2-butene | 3 ml | 87.8 |
| 49 | B | Sodium borohydrate | 300 mg | 98.5 |

*A Eicosapentaenoic acid; B: Eicosapentaenoic acid ethyl ester

EXAMPLE 50

An aqueous solution in which 14 g of silver nitrate was dissolved in 8 ml of distilled water was added under an atmosphere of nitrogen in the dark to 10 g of a fatty acid mixture which contained 30% of docosahexaenoic acid and impurities such as palmitic acid. After stirring for 2 hours, the aqueous phase was obtained by separating from the fatty acid mixture. The resulting aqueous phase was washed twice with 100 ml of hexane and the resulting hexane phase was washed with distilled water and then with saturated saline and was dehydrated using magnesium sulfate. By concentration under reduced pressure, 1.81 g of a fatty acid fraction was obtained. Analysis of the fatty acid composition showed that docosahexaenoic acid having a purity of 67.3% was obtained. Furthermore, the docosahexaenoic acid having the 67.3% purity was purified in the same manner as described above. As a result, docosahexaenoic acid having a purity of 88.5% was obtained.

EXAMPLE 51

An aqueous solution in which 13 g of silver nitrate was dissolved in 8 ml of distilled water was added under an atmosphere of nitrogen in the dark to 15 g of a fatty acid mixture which contained 25% of eicosapentaenoic acid and impurities such as palmitic acid and the resulting mixture was stirred for 2 hours. 2.81 g of a fatty acid fraction was obtained by extraction and recovery using benzene in the same manner as described in Example 50. Analysis of the fatty acid composition showed that eicosapentaenoic acid having a purity of 85.2% was obtained. Furthermore, eicosapentaenoic acid having the 85.2% purity was. purified in the same manner as described above. As a result, eicosapentaenoic acid having a purity of 97.6% was obtained.

EXAMPLE 52

An aqueous solution in which 14 g of silver nitrate was dissolved in 8 ml of distilled water was added under an atmosphere of nitrogen in the dark to 10 g of a fatty acid mixture which contained 43% of arachidonic acid and impurities such as stearic acid and the resulting mixture was stirred for 2 hours. 3.01 g of a fatty acid fraction was obtained by extraction and recovery procedures using chloroform in the same manner as described in Example 50. Analysis of the fatty acid composition showed that arachidonic acid having a purity of 94.3% was obtained. Furthermore, the arachidonic acid having the 94.3% purity was purified in the same manner as described above. As a result, arachidonic acid having a purity of 98.6% was obtained.

EXAMPLE 53

An aqueous solution in which 25 g of silver nitrate was dissolved in 15 ml of distilled water was added under an atmosphere of nitrogen in the dark to 30 g of a fatty acid ethyl ester mixture which contained 42.3% of docosahexaenoic acid ethyl ester and impurities such as palmitic acid and the resulting mixture was stirred for 2 hours. After the reaction, the aqueous phase was isolated from the fatty acid ethyl ester mixture. The resulting aqueous phase was washed twice with 150 ml of benzene and the resulting benzene phase was washed with distilled water and then with saturated saline and was dehydrated using magnesium sulfate. By concentration under reduced pressure, 6.3 g of a fatty acid ethyl ester fraction was obtained. Analysis of the fatty acid ethyl ester composition showed that the purity of docosahexaenoic acid ethyl ester in the fraction was 96.4%.

EXAMPLE 54

An aqueous solution in which 2.5 g of silver nitrate was dissolved in 1.5 ml of distilled water was added under an atmosphere of nitrogen in the dark to 3.0 g of a fatty acid ethyl ester mixture which contained 30.6% of eicosapentaenoic acid ethyl ester and impurities such as stearic acid and the resulting mixture was stirred for 2 hours. 543 mg of a fatty acid methyl ester fraction was obtained by extracting and recovering using chloroform in the same manner as described in Example 53. Analysis of the fatty acid methyl ester composition showed that the purity of eicosapentaenoic acid methyl ester was 95.1%.

EXAMPLE 55

An aqueous solution in which 2.5 g of silver nitrate was dissolved in 1.5 ml of distilled water was added under an atmosphere of nitrogen in the dark to 3.0 g of a fatty acid ethyl ester mixture which contained 45.4% of arachidonic acid ethyl ester and impurities such as palmitic acid and the resulting mixture was stirred for 2 hours. 641 mg of a fatty acid ethyl ester fraction was obtained by extracting and recovering using ethyl acetate in the same manner as described in Example 53. Analysis of the fatty acid ethyl ester composition showed that the purity of arachidonic acid ethyl ester was 92.4%.

EXAMPLE 56

An aqueous solution in which 2.5 g of silver perchlorate was dissolved in 1.5 ml of distilled water was added under an atmosphere of nitrogen in the dark to 2.0 g of a fatty acid mixture which contained 35.5% of docosahexaenoic acid and impurities such as palmitic acid. After stirring for 2 hours, the aqueous phase was obtained by isolating the fatty acid mixture from the aqueous phase. The resulting aqueous phase was washed twice with 120 ml of hexane and the resulting hexane phase was washed with distilled water and then with saturated saline and was dehydrated using magnesium sulfate. By concentration under reduced pressure, 344 mg of a fatty acid fraction was obtained. Analysis of the fatty acid composition showed that the purity of docosahexaenoic acid was 90.4%.

EXAMPLE 57

An aqueous solution in which 2.5 g of silver nitrate was dissolved in 1.5 ml of distilled water was added under an atmosphere of nitrogen in the dark to 3.0 g of a fatty acid ethyl ester mixture which contained 56.8% of linoleic acid ethyl ester and impurities such as stearic acid and the resulting mixture was stirred for 30 minutes. Extraction and recovery were carried out using dichloromethane in the same manner as described in Example 53. 842 mg of a fatty acid ethyl ester fraction was obtained. Analysis showed that the purity of linoleic acid ethyl ester was 85.7%.

EXAMPLE 58

An aqueous solution in which 2.5 g of silver nitrate was dissolved in 1.5 ml of distilled water was added under an atmosphere of nitrogen in the dark to 2.7 g of a fatty acid ethyl ester mixture which contained 43.6% of α-linolenic acid ethyl ester and impurities such as stearic acid and the resulting mixture was stirred for 25 minutes. Extraction and recovery were carried out using chloroform in the same manner as described in Example 53. 763 mg of a fatty acid ethyl ester fraction was obtained. Analysis showed that the purity of α-linolenic acid ethyl ester was 90.4%.

EXAMPLE 59

An aqueous solution in which 25.50 g of silver nitrate was dissolved in 10 ml of distilled water was added to 20.85 g of a fatty acid ethyl ester mixture which contained 60% of eicosapentaenoic acid ethyl ester and impurities such as erucic acid ethyl ester and the resulting mixture was stirred at 3° C. for one hour under an atmosphere of nitrogen in the dark. After stirring, the reaction mixture was washed twice with 20 ml of hexane and the aqueous phase was recovered. The recovered aqueous phase was stirred at 90° C. for one hour under a nitrogen atmosphere in the dark and the oil phase was recovered. 20 ml of hexane was added to and dissolved in the recovered oil phase and the resulting solution was washed twice with 20 ml of distilled water and then with 10 ml of saturated saline and was dehydrated using magnesium sulfate. By concentration under reduced pressure, 3.75 g of a fatty acid ethyl ester fraction was obtained. Analysis of the fatty acid ethyl ester composition showed that the purity of eicosapentaenoic acid ethyl ester was 85.6%.

EXAMPLE 60

An aqueous solution in which 848 mg of silver nitrate was dissolved in 0.5 ml of distilled water was added to 1.006 g of a fatty acid mixture which contained 59% of eicosapentaenoic acid and impurities such as erucic acid and the resulting mixture was stirred at 3° C. for 30 minutes under an atmosphere of nitrogen in the dark. After stirring, the reaction mixture was washed twice with 10 ml of hexane and the aqueous phase was recovered. To the recovered aqueous phase was added 40 ml of hexane, and the mixture was refluxed for one hour under a nitrogen atmosphere in the dark. The hexane phase was recovered and was washed twice with 20 ml of distilled water and then with 10 ml of saturated saline and was dehydrated using magnesium sulfate. By concentration under reduced pressure, 143 mg of a fatty acid fraction was obtained. Analysis of the fatty acid composition showed that the purity of eicosapentaenoic acid was 95.8%.

EXAMPLE 61

An aqueous solution in which 585 mg of silver acetate was dissolved in 0.5 ml of distilled water was added to 1.012 g of a fatty acid mixture which contained 60% of docosahexaenoic acid and impurities such as erucic acid and the resulting mixture was stirred at −5° C. for one hour under an atmosphere of nitrogen in the dark. After stirring, the reaction mixture was washed twice with 10 ml of hexane and the aqueous phase was recovered. To the recovered aqueous phase was added 10 ml of toluene, and the mixture was refluxed for one hour under a nitrogen atmosphere in the dark. The toluene phase was recovered and washed twice with 20 ml of distilled water and then with 10 ml of saturated saline and was dehydrated using magnesium sulfate. By concentration under reduced pressure, 70 mg of a fatty acid fraction was obtained. Analysis of the fatty acid composition showed that the purity of docosahexaenoic acid was 92.1%.

EXAMPLE 62

An aqueous solution in which 1.946 g of silver tetrafluoroborate was dissolved in 0.5 ml of distilled water was added to 1.001 g of a fatty acid mixture which contained 25% of arachidonic acid and impurities such as stearic acid and the resulting mixture was stirred at −2° C. for one hour under an atmosphere of nitrogen in the dark. After stirring, the reaction mixture was washed twice with 10 ml of hexane and the aqueous phase was recovered. To the recovered aqueous phase was added 10 ml of xylene and the mixture was heated at 100° C. for one hour under a nitrogen atmosphere in the dark. The xylene phase was recovered and washed twice with 20 ml of distilled water and then with 10 ml of saturated saline and was dehydrated using magnesium sulfate. By concentration under reduced pressure, 96 mg of a fatty acid fraction was obtained. Analysis of the fatty acid composition showed that the purity of arachidonic acid was 89.0%.

EXAMPLE 63

An aqueous solution in which 1.037 g of silver perchlorate was dissolved in 0.5 ml of distilled water was added to 2.001 g of a fatty acid mixture which contained 20% of γ-linolenic acid and impurities such as oleic acid and the resulting mixture was stirred at 4° C. for one hour under an atmosphere of nitrogen in the dark. After stirring, the reaction mixture was washed twice with 10 ml of hexane and the aqueous phase was recovered. To the recovered aqueous phase was added 10 ml of toluene, and the mixture was heated at 90° C. for one hour under a nitrogen atmosphere in the dark. The toluene phase was recovered and was washed twice with 20 ml of distilled water and then with 10 ml of saturated saline and was dehydrated using magnesium sulfate. By concentration under reduced pressure, 75 mg of a fatty acid fraction was obtained. Analysis of the fatty acid composition showed that the purity of gamma-linolenic acid was 90.5%.

EXAMPLE 64

An aqueous solution in which 1.021 g of silver perchlorate was dissolved in 0.5 ml of distilled water was added to 1.021 g of a fatty acid mixture which contained 600% of alpha-linolenic acid and impurities such as oleic acid and the resulting mixture was stirred at 4° C. for one hour under an atmosphere of nitrogen in the dark. After stirring, the reaction mixture was washed twice with 10 ml of hexane and the aqueous phase was recovered. To the recovered aqueous phase was added 10 ml of toluene, and the mixture was heated at 90° C. for one hour under a nitrogen atmosphere in the dark. The toluene phase was recovered and was washed twice with 20 ml of distilled water and then with 10 ml of saturated saline and was dehydrated using magnesium sulfate. By concentration under reduced pressure, 112 mg of a fatty acid fraction was obtained. Analysis of the fatty acid composition showed that the purity of alpha-linolenic acid was 93.0%.

Examples of the apparatus for purification in accordance with the present invention are shown as follows: The purities of eicosapentaenoic acid ethyl ester (EPA-Et) and docosahexaenoic acid ethyl ester (DHA-Et) used as starting materials were 55.4% and 52.3%, respectively. Furthermore, impurities which were contained in these materials were mainly fatty acid ethyl esters having a saturation index less than 3, such as palmitic acid, oleic acid and linoleic acid.

EXAMPLES 65 to 68

[Examples with the use of bulk liquid membranes]

Figure 1B:
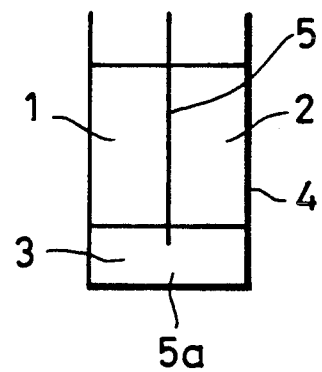

Isolation was carried out using a bulk liquid membrane apparatus (made of acrylic resin, having an inner size of 20 mm ×20 mm and a height of 100 mm) shown in FIG. 1. Further, in all through the examples 65 to 68, the ratio of a solvent (heptane) to a liquid membrane (a silver nitrate solution) was 3:1 by volume, and the operation was carried out at 25° C. for 6 hours.

The results are summarized in Table 2. In Table 2, the purity represents that of EPA-Et in the recovered fatty acid fraction and the recovery represents the rate of EPA-Et found in the recovered fatty acid fraction to EPA-Et supplied in the starting material.

TABLE 2

| | Examples with the use of bulk membranes | | | |
|---|---|---|---|---|
| Examples | Concentration of silver nitrate (g/l) | Fatty acid concentration in starting material (g/l) | EPA-Et (%) Purity | Recovery |
| 65 | 170 | 302 | 94.1 | 18.5 |
| 66 | 255 | 302 | 95.5 | 38.4 |
| 67 | 340 | 302 | 95.2 | 40.7 |
| 68 | 255 | 151 | 95.3 | 37.9 |
| Comparative Example | 0 | 302 | — | 0.0 |

As evidently shown in Table 2, the isolation of EPA-Et was carried out highly selectively when the silver nitrate solution was used as the liquid membrane. On the other hand, as shown in Comparative Example, EPA-Et was not at all isolated when the liquid membrane did not contain any silver nitrate.

EXAMPLES 69 to 72

[Examples with the use of supported liquid membranes]

Isolation was carried out using a flat sheet membrane-type supported liquid membrane apparatus (having a membrane size of 60 mm ×60 mm) shown in FIG. 2. A solution of silver nitrate was used as the liquid membrane. A membrane filter made of polyvinylidene difluoride (a product of Japan Millipore Limited, hydrophilic Durapore; pore diameter: 0.22 micrometer, porosity: 75%, thickness: 150 micrometers) was used for a membrane which was impregnated with the silver nitrate solution. A heptane solution, a starting material containing docosahexaenoic acid ethyl ester (DHAEt), was supplied at a flow rate of 0.3 ml/min to one side of the flow channel of the apparatus and heptane for recovery was simultaneously supplied at the same flow rate to the other side of the channel of the apparatus. From one hour after, sampling was carried out to measure the amount and the composition of the fatty acid fractions contained in the heptane phase in the recovery side.

As evidently shown in Table 3, in which the results were summarized, the isolation of DHA-Et was carried out highly selectively when the silver nitrate solution was used as the liquid membrane.

TABLE 3

| | Examples with the use of supported liquid membranes | | | |
|---|---|---|---|---|
| | Concentration of silver | Fatty acid concentration in starting | DHA-Et (%) | |
| Examples | nitrate (g/l) | material (g/l) | Purity | Recovery |
| 69 | 170 | 328 | 95.3 | 15.2 |
| 70 | 340 | 328 | 96.5 | 36.3 |
| 71 | 850 | 328 | 96.3 | 41.2 |
| 72 | 340 | 164 | 95.3 | 34.4 |

We claim:

1. A method of purifying a fatty acid-related polyunsaturated compound, which is characterized in that the following four steps are carried out in numerical order:
   1) an aqueous medium containing a silver salt is brought into contact with a mixture containing the fatty acid-related unsaturated compound to form a silver complex of the fatty acid-related polyunsaturated compound;
   2) the silver complex is separated from a fraction in which no silver complex was formed and is subjected to procedures for dissociation of the silver
   3) the fatty acid-related polyunsaturated compound is dissociated from the silver complex; and
   4) the dissociated fatty acid-related polyunsaturated compound is isolated.

2. The method as set forth in claim 1, wherein a concentration of the silver salt contained in the aqueous medium is 0.1 mol or more per liter.

3. The method as set forth in claim 2, wherein the step 1) is carried out in a mixed system comprising an aqueous medium containing the said mixture and a silver salt.

4. The method as set forth in claim 3, wherein the step 2) comprises fractionation of the aqueous medium phase from the oil phase in the said mixed system.

5. The method as set forth in claim 4, wherein the step 3) comprises addition of a dissociating to the fractionated aqueous medium phase.

6. The method as set forth in claim 4, wherein the step 3) comprises dilution of the fractionated aqueous medium phase.

7. The method as set forth in claim 4, wherein the step 3) comprises heating of the fractionated aqueous medium phase.

8. The method as set forth in claim 5, 6 or 7, wherein a solvent in which a fatty acid-related polyunsaturated compound is soluble is allowed to coexist in the system in the step 3).

9. The method as set forth in claim 4, wherein the step 3) comprises bringing a fat-soluble medium to contact with the fractionated aqueous medium phase.

10. The method as set forth in claim 2, wherein the step 3) comprises formation of a liquid membrane contact surface between the said mixture and the aqueous medium containing the silver salt.

11. The method as set forth in claim 9, wherein the liquid membrane is formed via a supported liquid membrane which is formed by impregnating a hydrophilic porous material with the aqueous medium containing the silver salt.

12. The method as set forth in claim 9, wherein in the system in which the mixture and the fat-soluble medium are each separated from the aqueous medium containing the silver salt to form a primary and a secondary liquid membrane contact surface, the step 2) is carried out by transporting a substance inside the aqueous medium containing the silver salt of the silver complex and the step 3) is carried out on the secondary liquid membrane contact surface.

13. The method as set forth in claim 10 or 11, wherein the fluid inside of the aqueous medium containing the silver salt is gently flown not to destroy the contact surface of the liquid membrane.

* * * * *